United States Patent [19]

Palumbo et al.

[11] Patent Number: 5,262,223
[45] Date of Patent: Nov. 16, 1993

[54] ABSORBENT ELEMENT AND AN ABSORBENT ARTICLE INCLUDING THE ELEMENT

[75] Inventors: Gianfranco Palumbo, Pescara; Giovanni Carlucci, Chieti; Remo Di Girolamo, Pescara, all of Italy

[73] Assignee: Faricerca S.p.A., Pescara, Italy

[21] Appl. No.: 887,655

[22] Filed: May 26, 1992

Related U.S. Application Data

[63] Continuation of Ser. No. 440,140, Nov. 22, 1989, abandoned.

[30] Foreign Application Priority Data

Nov. 25, 1988 [IT] Italy .................. 68057 A/88

[51] Int. Cl.$^5$ ............................................. B32B 3/00
[52] U.S. Cl. ........................... 428/195; 428/198; 428/206; 428/283; 428/284; 428/323; 428/913; 604/367; 604/368
[58] Field of Search ............... 428/195, 198, 283, 284, 428/326, 913, 323; 604/367, 368

[56] References Cited

U.S. PATENT DOCUMENTS

| | | | |
|---|---|---|---|
| Re. 32,649 | 4/1988 | Brandt et al. | 604/368 |
| 4,297,410 | 10/1981 | Tsuchiya et al. | 428/283 |
| 4,413,995 | 11/1983 | Korpman | 604/368 |
| 4,429,001 | 1/1984 | Kolpin et al. | 428/296 |
| 4,578,068 | 3/1986 | Kramer et al. | 428/283 |
| 4,676,784 | 6/1987 | Erdman et al. | 604/358 |
| 4,699,823 | 10/1987 | Hellenberger et al. | 428/283 |
| 4,834,735 | 5/1989 | Alemany et al. | 428/283 |

FOREIGN PATENT DOCUMENTS

| | | |
|---|---|---|
| 146190 | 6/1985 | European Pat. Off. |
| 160572 | 9/1987 | European Pat. Off. |
| WO87/05860 | 10/1987 | PCT Int'l Appl. |

*Primary Examiner*—James J. Bell
*Attorney, Agent, or Firm*—Sughrue, Mion, Zinn, Macpeak & Seas

[57] ABSTRACT

An absorbent element for absorbent articles comprised of hydrophilic fibers and a discontinuous, non-uniform layer of particles of absorbent hydrogelling material arranged on the upper surface of the element includes a deposition zone on which the absorbent hydrogelling material is distributed with an increased surface density.

The zone of increased surface density of the absorbent hydrogelling material can preferably be located in different positions suitable for the different anatomical forms of the users, so as to ensure more effective sealing against the backflow of the liquid and thus ensure an improved feeling of dryness.

20 Claims, 4 Drawing Sheets

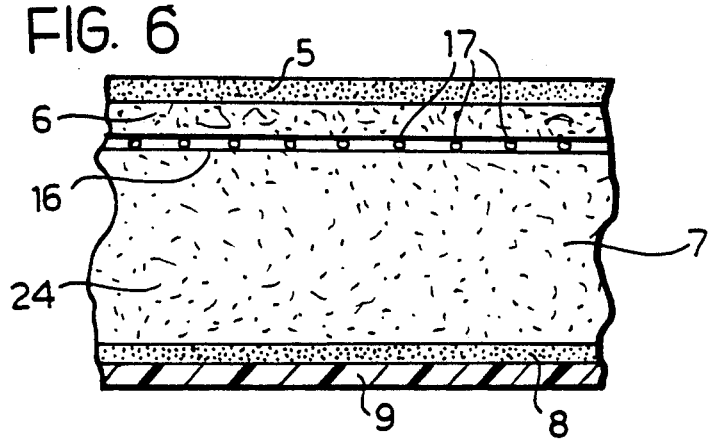
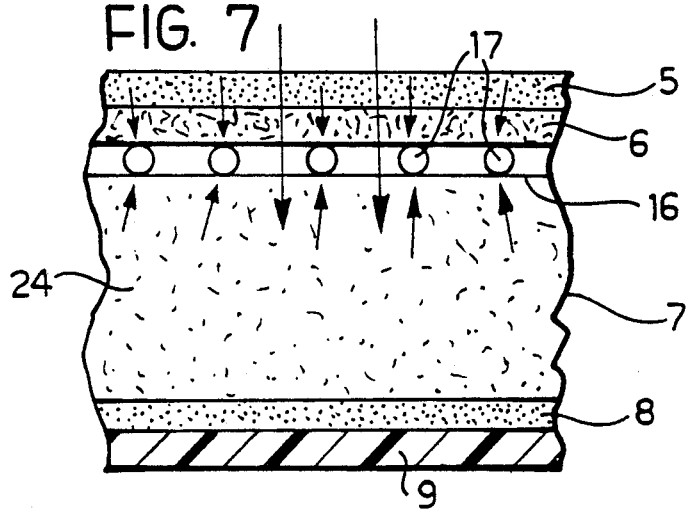
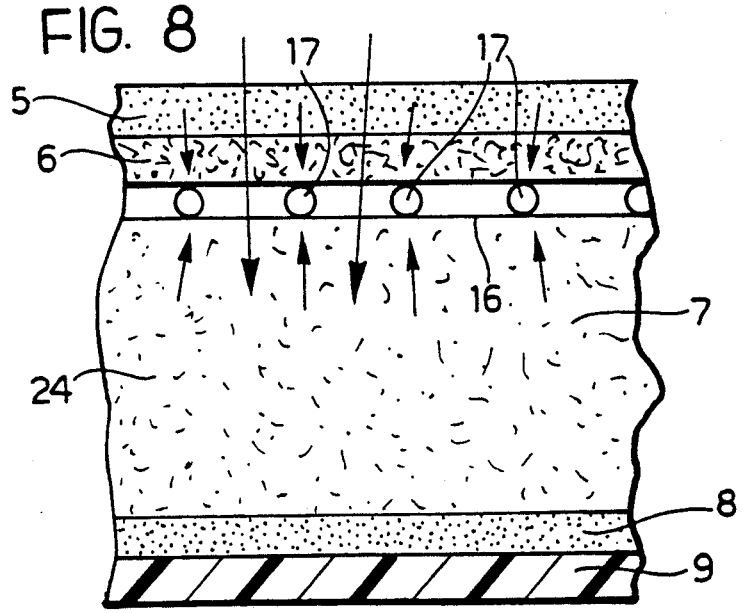

ABSORBENT ELEMENT AND AN ABSORBENT ARTICLE INCLUDING THE ELEMENT

This is a continuation of application Ser. No. 07/440,140 filed Nov. 22, 1989 is now abandoned.

DESCRIPTION

1. Field of the Invention

The present invention relates to absorbent elements made from hydrophilic fibres, for examples cellulose fibres, in which the surface facing the user has a discontinuous layer of particles of an absorbent hydrogelling material.

In particular, the present invention relates to an improved absorbent element which can provide the user with an improved feeling of dryness by virtue of the presence of the discontinuous layer of hydrogelling particles.

2. Description of the Prior Art

Disposable absorbent articles, such as babies' diapers, pads for incontinent adults, sanitary towels and similar products, are well known and are all provided with an absorbent element for absorbing and retaining body fluids.

Such absorbent element, commonly known as pad, must be able to take up the liquid rapidly and distribute it internally to avoid leakage at the sides; furthermore, it must have the capacity to retain the fluids when subjected to the normal pressures of use.

Absorbent pads made of cellulose fibres derived from conifer wood and bleached by a chemical process have satisfactory characteristics as regards the rate of absorption and distribution of the liquid, but are not very efficient from the point of view of retention and may allow liquid to flow back from the absorbent structure under the normal pressures of use.

One possible method of preventing this problem is to increase considerably the quantity of absorbent material in the pad so that the liquid does not flow back under the normal pressures of use; however, the fact that the cellulose is very hydrophilic means that in any event the surface of the absorbent pad tends to remain damp and can thus cause the user to feel wet.

An attempt has been made to resolve the liquid-backflow problem by mixing particles of absorbent hydrogelling material with the cellulose in order to increase the absorption and retention capacities of the absorbent element.

For example, European Patent Application No. EP-A-0 122 042 proposes very dense absorbent structures constituted by a uniform mixture of particles of hydrogelling material and cellulose fibres.

The hydrogelling materials, commonly known as superabsorbents, are polymers which can absorb a large quantity of liquid, water or body fluids relative to their weight and can retain the fluids even under moderate pressure; because of these characteristics, their use in disposable absorbent articles has been proposed for some time.

Their good absorption capacity, however, is not matched by an equally good absorption rate and this can have an adverse effect on the performance of absorbent articles incorporating these substances.

In fact, superabsorbents can give rise to a phenomenon known as "gel blocking"; when superabsorbent particle comes into contact with the liquid, its outer surface starts to absorb and swells, obstructing the passage of the liquid into the particles; the liquid can only penetrate further into the still-dry core of the particles by means of a very slow diffusion mechanism.

This phenomenon not only prevents full use from being made of the large absorption capacities of superabsorbent substances, but can also involve a decrease in the absorption rate of structures with superabsorbent mixed with fibers, resulting in the possibility of lateral leakages.

Finally, although the superabsorbent substances have the advantage over cellulose fibres that they securely retain the liquids absorbed, the use of such substances simply mixed with cellulose fibres presents problems.

The many attempts of the prior art to resolve the problem have lead to the production of various devices using superabsorbents mixed with hydrophilic fibres.

European Patent Application No. EP-A-0 254 476 in the name of Procter and Gamble proposes a low-density zone positioned in the absorbent pad so as to receive the liquid directly upon its release; this zone constitutes a kind of temporary storage sump for the liquid which must then be absorbed into the surrounding denser zones of the pad.

A substantially different approach to the solution of the liquid-backflow problem from that based on the use of superabsorbent mixed with fibres is described in U.S. Pat. No. 3,888,256 in the name of H. Studinger.

In this solution, the superabsorbent is located only on the surface of a conventional pad; the quantity used is such that, as the particles absorb and swell, they penetrate each other to form a continuous layer on top of the pad which prevents the liquid from flowing back under normal conditions of use; however, this layer also obstructs the absorption of further quantities of liquid which may be released subsequently.

There is thus a need for an absorbent element which rapidly absorbs and distributes the liquid, minimizing the risks of backflow and making adequate use of the characteristics of the absorbent hydrogelling substances.

OBJECTS AND SUMMARY OF THE INVENTION

The object of the present invention is to avoid the problems described by virtue of an absorbent element of hydrophilic fibres, characterised in that the element has a discontinuous layer of absorbent hydrogelling material, preferably distributed non-uniformly, on its surface which faces the user's body.

Further advantages and characteristics of the invention form the subjects of the claims which follow the present description.

DETAILED DESCRIPTION OF THE INVENTION

Further characteristics and advantages of the invention will become clear from the description which follows with reference to the appended drawings, provided by way of non-limiting example, in which:

FIG. 6 is a sectional view of a portion of the diaper incorporating the absorbent element of the present invention, on an enlarged scale;

FIG. 7 is a sectional view similar to that of FIG. 6 but showing the absorbent element during the absorption of a certain quantity of liquid, and FIG. 8 is yet another sectional view similar to that of FIG. 6, showing the absorbent element during the absorption of a further quantity of liquid.

The absorbent elements of the present invention will be described with reference to their use in disposable absorbent articles; these articles are worn by the user in direct contact with the body, for the purpose of absorbing body fluids, and are subsequently thrown away after a single use.

Figure 1:
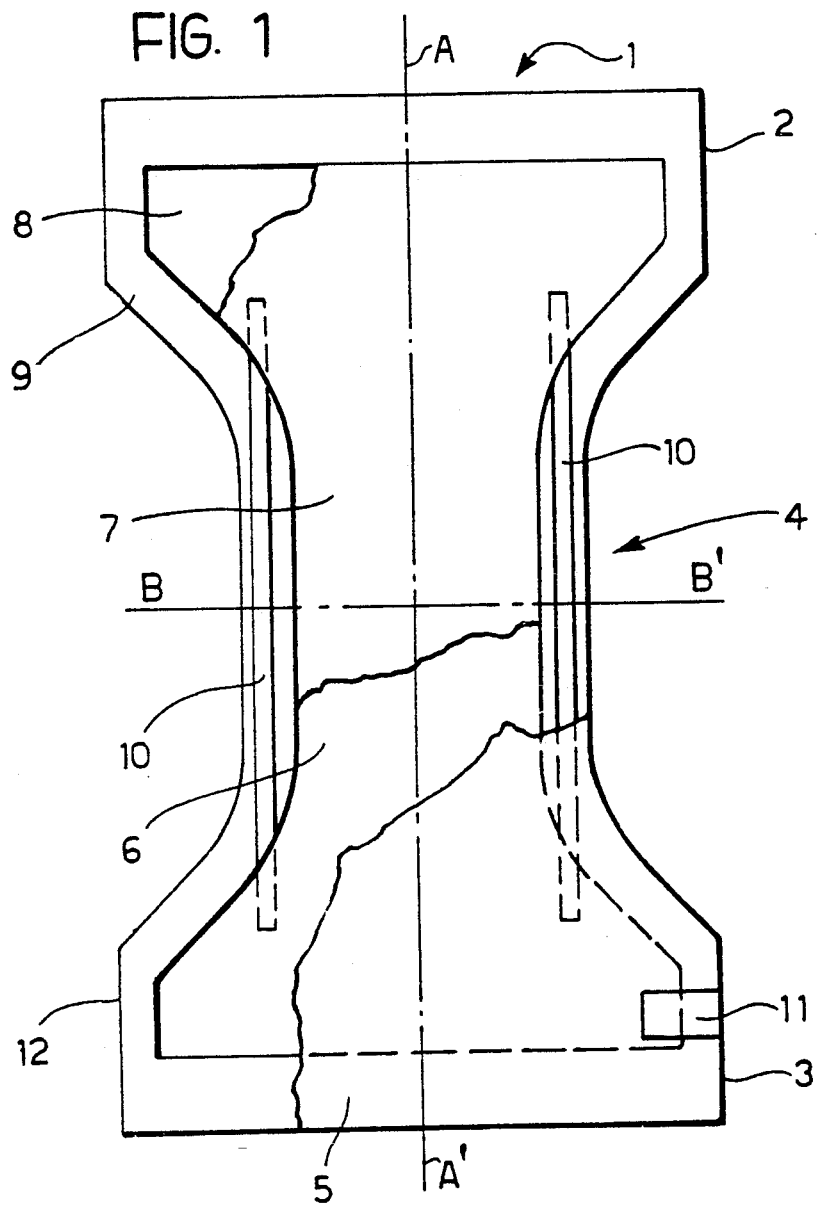
FIG. 1 is a plan view of a disposable diaper produced according to the present invention.

The disposable baby's diaper 1 shown in FIG. 1 represents a preferred embodiment of an absorbent article according to the present invention, but the present invention is also intended to apply to other disposable absorbent articles, such as products for the incontinent, sanitary towels and the like.

FIG. 1 is a plan view of a diaper in its stretched out configuration with some portions of the structure eliminated in order to show the construction of the diaper more clearly; in particular, the side of the diaper which comes into contact with the user is shown.

FIG. 1 shows two end regions, a front region 2 and a rear region 3, which in use are positioned around the user's waist, and a central region 4 situated between them; a longitudinal axis AA' and a transverse axis BB' can also be seen.

The diaper includes an upper layer 5 of nonwoven fabric which is permeable to liquids and is intended to come into direct contact with the user's skin, a layer 6 of tissue immediately beneath the nonwoven fabric, an absorbent element 7, a second layer 8 of tissue, an impermeable plastics layer 9, and elastic elements 10 situated on either side of the absorbent element 7 in correspondence with its central region for effecting a seal around the legs of the user in use: one of the two adhesive tabs 11 necessary for fastening the diaper can also be seen on the rear region 3.

The outermost layers 5 and 9 of nonwoven fabric and plastics have the same shape and dimensions, corresponding to the outline 12 of the whole diaper, whilst the two tissue layers 6 and 8 are preferably shaped like the absorbent element 7 between them.

Figure 3:
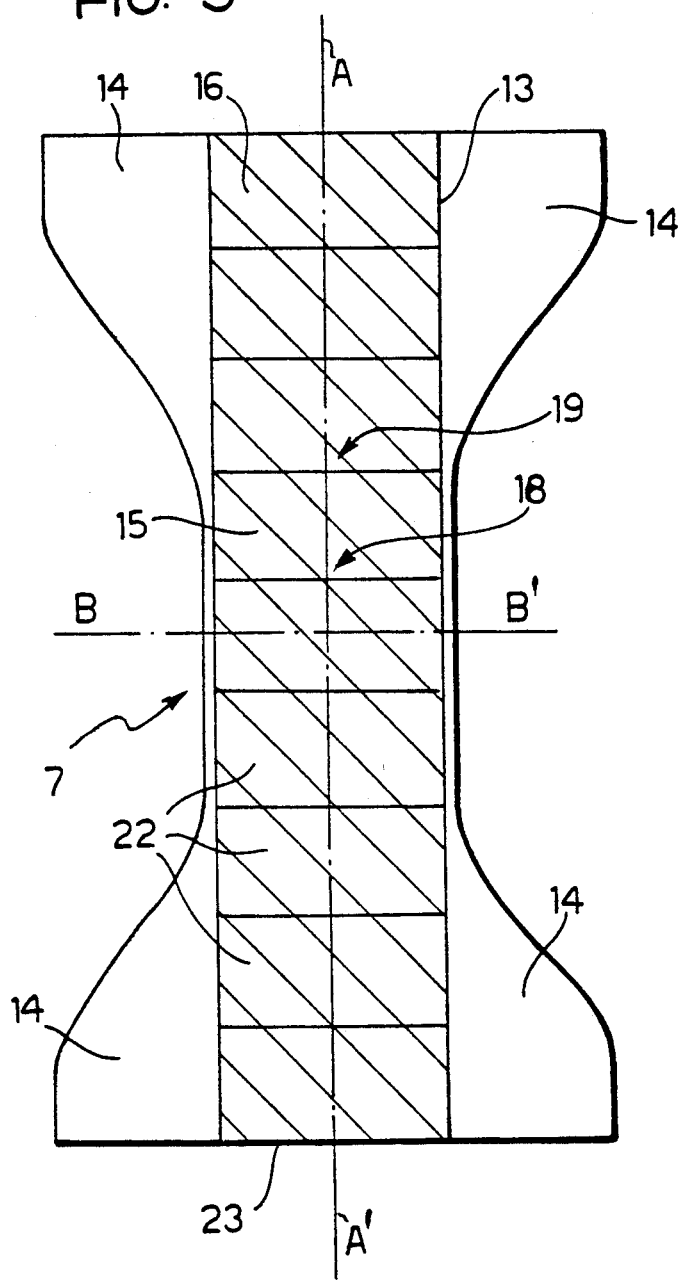
FIG. 3 is a plan view showing only the absorbent element of the diaper of FIG. 1, two possible non-uniform distributions of the superabsorbent of which are shown in FIGS. 4 and 5.

In the configuration shown, the absorbent element 7 is hourglass-shaped; in FIG. 3, where it is shown on its own, it is easy to distinguish a central rectangular zone 13, with a length equal to the length of the element itself and a width approximately equal to its minimum width, and four peripheral zones 14, known as ears, situated on either side of the rectangular zone in correspondence with the two longitudinal ends of the absorbent element. The rectangular zone 13 includes the portion 15 of the absorbent element which is intended to receive the flow of liquid first since, in use, it is situated nearest the point from which the liquid is discharged; this zone can be referred to as a deposition zone.

The absorbent element 7 is composed solely of hydrophilic fibres 24, preferably of cellulose pulp.

Figure 2:
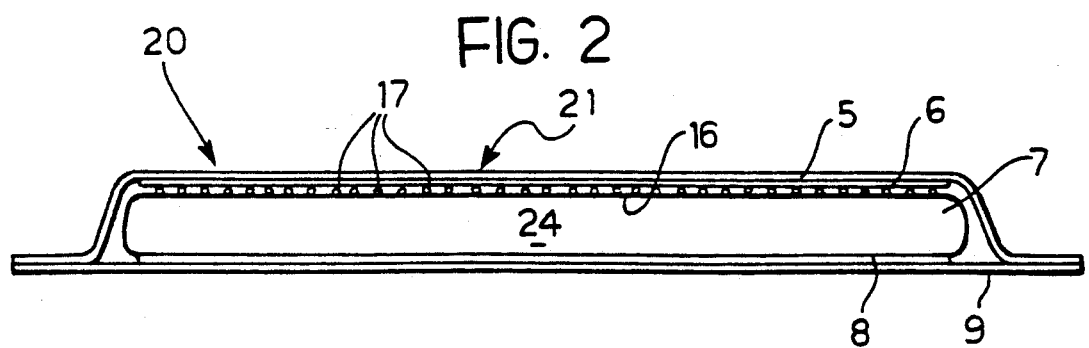
FIG. 2 is a sectional view of the diaper taken on the longitudinal axis A—A' of FIG. 1.

FIG. 2 shows that particles 17 of absorbent hydrogelling material are distributed non-continuously and preferably non-uniformly on the upper surface 16 of the absorbent element 7, preferably only in correspondence with the rectangular central zone 13 shown in FIG. 3.

Suitable absorbent hydrogelling substances may be inorganic or organic materials, such as cross-linked polymers wholly known in the art; preferably, the Chemische Fabrik Stockhausen superabsorbent product with the trade name Favor Sab 922 is used.

The average size of the particles 17, that is, the weighted average of the smallest dimension of the individual particles, may be between 100 and 800 microns, preferably between 200 and 500 microns.

The surface distribution of the superabsorbent particles 17 must be discontinuous, that is, such as to ensure that the particles are substantially isolated from each other before they absorb the liquid and that they remain so even after the swelling which results from the absorption, or, at any rate, that they do not form a continuous layer on the surface of the pad as they swell.

In general, this result is achieved with a surface distribution of particles 17 of the preferred dimensions at a density of between 5 $g/m^2$ and 70 $g/m^2$, preferably between 10 $g/m^2$ and 60 $g/m^2$.

In order to improve the performance of the absorbent element 7 of the present invention, the surface distribution of the superabsorbent is preferably non-uniform, a larger quantity being located in the deposition zone 15 of the pad, which has already been defined as the zone intended to receive the flow of liquid first since, in use, it is nearest to the point from which the liquid is discharged.

From an analysis carried out on normal diapers after use by plotting their absorption stains, it can be found that, because of the different anatomical forms of baby boys and baby girls, on average, the centre of the zone of the pad which first receives the flow of liquid may be located 55% of the way along the longitudinal axis AA' from the rear end, with respect to the total length of the pad, for girls and 65% of the way along for boys, as shown at 18 and 19 respectively in FIG. 3.

The superabsorbent layer on the surface of the pad can thus be formed with a different non-uniform distribution for baby boys and baby girls which is particularly suitable for their different anatomical forms.

Although, in principle, the surface distribution of the superabsorbent may vary along both axes of the pad, the surface density of the particles 17 in a preferred embodiment depends solely on their position along the longitudinal axis AA' and, at any point on that axis, is constant for the whole width of the zone 13 where the superabsorbent 17 is deposited.

Figure 4:
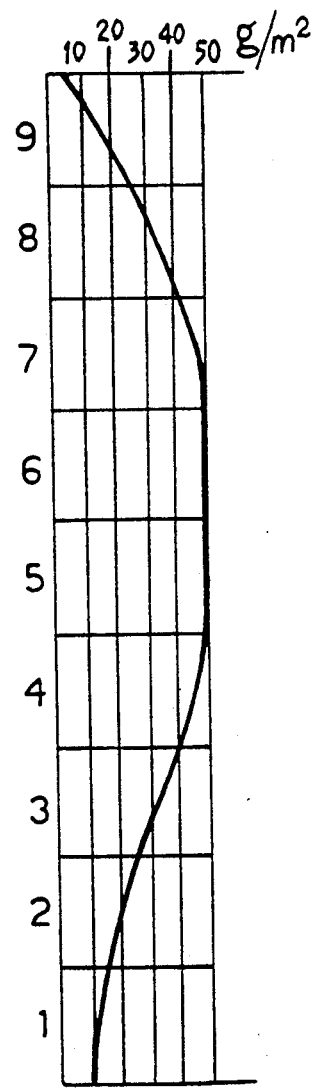
Figure 5:
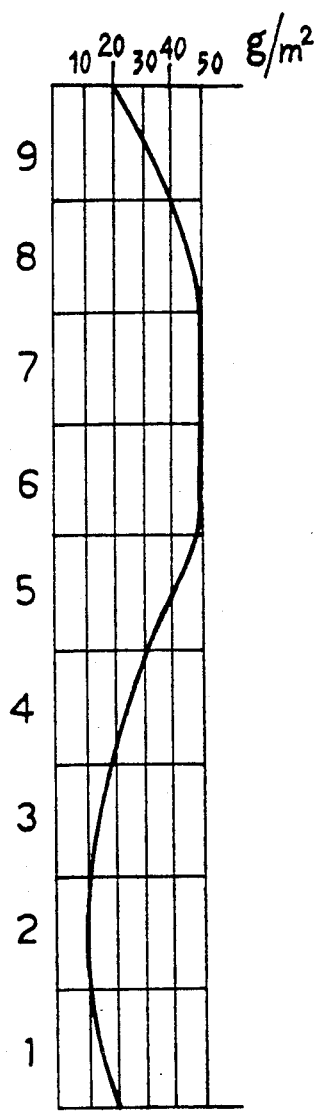

The surface distribution of the superabsorbent may vary gradually of discontinuously, along the longitudinal axis AA'; in the preferred configurations shown in FIGS. 4 and 5, the variation takes place along a continuous curve.

The extent of the portion 15 of the upper surface 16 of the pad 17 with a greater-than-average distribution of superabsorbent may be between 20% and 70% of the total surface of the zone with superabsorbent; the centre of the zone may be located on the longitudinal axis AA' of the pad at a distance of between 45% and 60% of the total length from the rear end 23 for diapers intended for girls and of between 60% and 70% of the total length for diapers intended for boys.

The center of the zone with a greater surface density of superabsorbent preferably coincides with the center of the deposition zone and is therefore located at points 55% (18) and 65% (19) of the way along the longitudinal axis AA' of the pad 7 for girls and for boys respectively.

FIG. 2 shows that, compared with the average value of the surface density of the superabsorbent, there are zones 20 of lesser density and a zone 21 of greater density, corresponding to the deposition zone 15; the relative density values of the various zones must in any case fall within the lower and upper limits given above.

FIGS. 4 and 5 show the two preferred, non-uniform distributions of the superabsorbent particles 17 on the rectangular central zone 13 of the pad 7; this zone is shown divided into nine equal parts 22 along the longitudinal axis AA', whilst the graph on the right is a curve showing the distribution of the particles in $g/m^2$ as a function of the length of the zone.

FIG. 4 shows the distribution suitable for girls' diapers: the centre 18 of the deposition zone 15 is on the longitudinal axis AA' at a distance of 55% of the total length of the pad from the rear end 23, with a maximum surface density of the superabsorbent of 50 $g/m^2$.

FIG. 5, on the other hand, shows the distribution suitable for boys' diapers, which differs from the above in that the centre 19 of the deposition zone 15 is located 65% of the way along the total length of the pad 7 from the rear end 23.

In both cases, the deposition zone 15 represents approximately 55% of the upper surface of the pad on which the superabsorbent is distributed and which, in the configuration illustrated, corresponds to the central rectangular zone 13.

The way in which the absorbent structure described above functions can be shown by means of FIGS. 6 to 8: FIG. 6 shows, in section, the initial configuration of a portion of the diaper.

At the moment when liquid is first released, the superabsorbent particles 17 start to swell slowly, while most of the liquid is absorbed by the fibers of the underlying pad 7: in FIG. 7, the main flow of liquid into the absorbent element 7 is shown by the larger arrows.

As they swell, the particles 17 substantially do not come into contact with each other and the aforementioned problem of the formation of a continuous layer of gelled superabsorbent which acts as a barrier to any subsequently released liquid is thus avoided; at the same time, the increase in volume of the particles 17 tends to lift the overlying layers of tissue 6 and nonwoven fabric 5 from the damp upper surface 16 of the pad 7.

The low absorption rate typical of the superabsorbent and the preferred, fairly large dimensions of the particles 17 mean that the particles are not saturated immediately but retain the capacity to absorb both the liquid still present in the layer of tissue 6, and possibly in the nonwoven fabric 5, and the liquid which may be squeezed out of the cellulose pad 7 and which tends to flow back to the surface because of the normal pressures to which the pad may be subjected in use; the secondary flows of liquid towards the particles 17, which are set up in use within the structure from the tissue 6, the nonwoven fabric 5 and the absorbent element 7 are represented by the smaller arrows in FIG. 7.

The diaper 1 of the present invention can therefore provide the user with a greater feeling of dryness by virtue of the double effect of the superabsorbent particles 17 which, as they swell, tend to lift the tissue 6 and the nonwoven fabric 5 from the wet surface 16 of the pad 7, isolating it therefrom, and which, moreover, can still absorb any liquid which flows back from the pad 7 towards the outside under pressure since they are not completely saturated with liquid. Moreover, the different non-uniform distribution of the superabsorbent diapers intended for boys and for girls provides a greater quantity of superabsorbent where it is most needed, that is, in correspondence with the deposition zones 15 which are situated differently for the two sexes.

The absorbent element 7 of the present invention has an improved capacity, even in the event of further releases of liquid by the user, as occurs, for example, when a diaper is worn through the night; FIG. 8 shows that the superabsorbent particles 17 arranged discontinuously on the surface 16 of the pad remain separate from each other as they swell; the liquid can therefore always pass easily between the particles 17 towards the underlying pad 7 of cellulose fibres 24, as indicated by the larger arrows. The smaller arrows here also show the secondary flows of liquid towards the superabsorbent particles 17 which still retain a residual absorption capacity.

The absorbent element 7 of the present invention can therefore make full use of the characteristics of the material of which it is made: the cellulose fibres 24 confer speed of absorption and absorption capacity, whilst the superabsorbent particles 17 provide a retention capacity against the backflow of liquid; moreover, the non-uniform surface distribution of the superabsorbent, which is different in the diapers intended for the two sexes, contributed to the provision of an improved feeling of dryness for both boys and girls.

The behaviour of the diapers produced according to the present invention as regards the backflow of liquid under normal pressures of use has been verified by a series of laboratory tests using, for comparison, diapers with the same characteristics but without the superabsorbent.

All the diapers used had hourglass-shaped cellulose fibre pads with an average bulk of approximately 10 $cm^3/g$; the pads were 460 mm long, 290 mm wide at the front and rear ends, and 135 mm wide in the central region; the total weight of cellulose was 63 g.

The upper, liquid-permeable layer was of a continuous-thread, nonwoven fabric of hydrophobic polypropylene fibre about 0.180 mm thick and weighing approximately 23.00 $g/m^2$.

The intermediate layers placed between the nonwoven fabric layer and the absorbent element, and between said absorbent element and the plastics layer were made from a wet strength tissue about 0.080 mm thick and weighing about 19.00 $g/m^2$; the plastics layer was a liquid-impervious polyethylene film about 0.025 mm thick and weighing approximately 24.30 $g/m^2$.

The diapers with the superabsorbent were of the girls' type with and average quantity of superabsorbent on the entire surface of the central rectangular zone of the pad of approximately 35 $g/m^2$ distributed non-uniformly in the manner described: the deposition zone, characterised by a greater-than-average surface density of superabsorbent, was about 230 mm long; the highest density of superabsorbent, which was approximately 50 $g/m^2$, covered an area about 100 mm long in the deposition zone.

The centre of the deposition zone was situated 250 mm along the longitudinal axis of the pad from its rear end.

All the diapers were without elastics so that they could be laid flat.

The superabsorbent was Chemische Fabrik Stockhausen's Favor Sab 922, as already mentioned, in granules with an average size of between 200 and 500 microns.

A 1% solution of NaCl in distilled water was used as the liquid.

The test consisted of the pouring of 150 ml of solution onto the center of the deposition zone of the diapers with superabsorbent on the surface and onto the center of the pad of the control diapers without a deposition zone with distinguishing characteristics, over a period of 7 sec.

Then, 10 minutes, 20 min, 40 min, and 60 min after the administration of the liquid, the diapers were subjected to a single compression of 3.85 Kpa for a period of 3 sec, a previously-weighed sheet of absorbent paper of dimensions such as to cover the entire upper surface of the diaper having been interposed between the surface of the diaper and the weight; the sheet was white, absorbent, type "N" paper from Farini S. p. A.

As soon as the compression stage was completed, the sheet of absorbent paper was withdrawn and weighed again: the difference from the original weight corresponded to the quantity of liquid absorbed through the surface of the diaper, this being liquid which had been squeezed from the pad during the compression and had flowed back to the surface of the nonwoven fabric and which is responsible for the wet feeling noticed by the user in actual use.

The results of the test are summarised in the following table, where the values shown are the quantities of liquid absorbed by the paper, in grams:

| Type of diaper | Single compressions after a period of | | | |
|---|---|---|---|---|
| | 60' | 40' | 20' | 10' |
| Control diaper | 0.27 | 0.65 | 0.98 | 1.70 |
| Diaper according to the present invention | 0.00 | 0.00 | 0.01 | 0.09 |

As can be seen, compared to conventional diapers, the diapers provided with absorbent elements produced according to the present invention show a consistently improved behaviour as regards the prevention of the backflow of liquid.

We claim:

1. An absorbent element made from hydrophilic fibers, having a discontinuous layer of absorbent hydrogelling material non-uniformly distributed on an upper surface of said element which faces the user wherein a deposition zone is located on said upper surface of said element located between and spaced from opposite ends of said element with the absorbent hydrogelling material being distributed on said deposition zone with a surface density greater than the average value of the surface density over said element.

2. An absorbent element according to claim 1, wherein the density of said absorbent hydrogelling material distributed on the surface is between 5 g/m$^2$ and 70 g/m$^2$.

3. An absorbent element according to claim 1, wherein the density of said absorbent hydrogelling material distributed on the surface is between 10 g/m$^2$ and 60 g/m$^2$.

4. An absorbent element according to claim 2, wherein the center of said deposition zone is situated on the longitudinal axis (AA') of said absorbent element at a distance of between 45% and 70% of the total length of the pad from its rear end.

5. An absorbent element according to claim 1, wherein the extent of said deposition zone is between 20% and 70% of the total surface of the zone with the absorbent hydrogelling material.

6. An absorbent element according to claim 1, wherein the absorbent hydrogelling material is a polyacrylate.

7. An absorbent element according to claim 1, wherein the absorbent hydrogelling material is in the form of particles with an average size of between 100 microns and 800 microns.

8. An absorbent element according to claim 1, wherein the absorbent hydrogelling material is in the form of particles with an average size of between 200 microns and 500 microns.

9. An absorbent article including a lower, impermeable plastics sheet, an upper permeable sheet of nonwoven fabric, and an absorbent element made from hydrophilic fibers positioned between the plastics sheet and the nonwoven fabric sheet, wherein the absorbent element has a discontinuous layer of absorbent hydrogelling material non-uniformly distributed on an upper surface of said element which faces the user wherein a deposition zone is located on said upper surface of said element located between and spaced from opposite ends of said element with the absorbent hydrogelling material being distributed on said deposition zone with a surface density greater than the average value of the surface density over said element.

10. An absorbent article according to claim 9, wherein the density of said absorbent hydrogelling material distributed on the surface is between 5 g/m$^2$ and 70 g/m$^2$.

11. An absorbent article according to claim 9, wherein the density of said absorbent hydrogelling material distributed on the surface is between 10 g/m$^2$ and 60 g/m$^2$.

12. An absorbent article according to claim 9, wherein the center of said deposition zone is situated on the longitudinal axis (AA') of said absorbent element at a distance of between 45% and 70% of the total length of the pad from its rear end.

13. An absorbent article according to claim 9, wherein the extent of the deposition zone is between 20% and 70% of the total surface of the zone with the absorbent hydrogelling material.

14. An absorbent article according to claim 9, wherein the absorbent hydrogelling material is a polyacrylate.

15. An absorbent article according to claim 9, wherein the absorbent hydrogelling material is in the form of particles with an average size of between 100 microns and 800 microns.

16. An absorbent article according to claim 9, wherein the absorbent hydrogelling material is in the form of particles with an average size of between 200 microns and 500 microns.

17. An absorbent article according to claim 9, wherein the center of the deposition zone is located on the surface of the absorbent element on the longitudinal axis (AA') of the absorbent element at a distance of between 45% and 60% of the total length from the rear end.

18. An absorbent article according to claim 17, wherein the center of the deposition zone is located at a distance of about 55% of the total length from the rear end.

19. An absorbent article according to claim 9, wherein the center of the deposition zone is located on the surface of the absorbent element on the longitudinal axis (AA') of the absorbent element at a distance of between 60% and 70% of the total length from the rear end.

20. An absorbent article according to claim 19, wherein the center of the deposition zone is located at a distance of about 65% of the total length from the rear end.

* * * * *